US00PP14510P29

(12) United States Plant Patent
McNaughton

(10) Patent No.: US PP14,510 P2
(45) Date of Patent: Feb. 3, 2004

(54) LAVANDULA PLANT NAMED 'LAVDEN 123'

(50) Latin Name: *Lavandula dentata*
Varietal Denomination: Lavden 123

(76) Inventor: Virginia McNaughton, Lavender Downs, Lawford Road, Christchurch (NZ)

( * ) Notice: Subject to any disclaimer, the term of this patent is extended or adjusted under 35 U.S.C. 154(b) by 0 days.

(21) Appl. No.: 10/404,302

(22) Filed: Mar. 31, 2003

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Susan B. McCormick

(57) ABSTRACT

A new cultivar of Lavandula plant named 'Lavden 123' that is characterized by a rounded bushy habit, long narrow flower spikes, purple sterile bracts and blue corollas. These traits set it apart from all other existing varieties of Lavandula known to the inventor.

2 Drawing Sheets

Genus: Lavandula.
Species: *dentata.*
Denomination: Lavden 123.

BACKGROUND OF THE INVENTION

The present invention relates to a new and distinct cultivar of lavender known botanically as *Lavandula dentata* and hereinafter referred to by the cultivar name 'Lavden 123'.

The new invention is a hybrid plant that resulted from the induced hybridization of the female parent plant *Lavandula dentata* and the male parent plant *Lavandula dentata*. Both parents were grey-leaved seedlings belonging to the breeder, and are no longer in existence. 'Lavden 123' was selected by the inventor in a cultivated area of Christchurch, New Zealand in January 2000.

'Lavden 123' grows to 70 centimeters in height and has a rounded, bushy habit. Under ideal growing conditions it is floriferous, with short to medium, uniform peduncles in a mature plant. The flower spikes are long and narrow with purple bracts and blue corollas while fertile bracts are tinged purple. 'Lavden 123' is susceptible to frost damage and will not grow in cold climates. Propagation can be accomplished by stem cuttings or tissue culture.

The new lavender plant 'Lavden 123' is distinct and unique due to its long narrow spikes, corolla color, sterile bract color, grey-green foliage and pronounced crenate leaf margins. The closest comparison plant is *Lavandula dentata* var. *candicans.*

The new invention was first asexually propagated by cuttings in 2000 by the inventor in a cultivated area of Christchurch, New Zealand. Since that time subsequent generations have been determined fixed and stable.

SUMMARY OF THE INVENTION

The following traits have been repeatedly observed and represent the distinguishing characteristics of the new lavender plant 'Lavden 123'. These traits in combination distinguish 'Lavden 123' from all other existing varieties of Lavandula known to the inventor. 'Lavden 123' has not been tested under all possible conditions and phenotypic differences may be observed with variations in environmental, climatic, and cultural conditions, however, without any variance in genotype.

1. Lavandula 'Lavden 123' exhibits a rounded, bushy habit.
2. Lavandula 'Lavden 123' exhibits long narrow fragrant flower spikes with purple sterile bracts and blue corollas.
3. Lavandula 'Lavden 123' exhibits short to medium, uniform peduncles.
4. Lavandula 'Lavden 123' exhibits fertile bracts that are tinged faintly purple.
5. Under ideal growing conditions Lavandula 'Lavden 123' is floriferous.
6. Lavandula 'Lavden 123' reaches 60–70 cm in height at maturity.
7. Lavandula 'Lavden 123' exhibits fragrant grey-green, crenate leaves.
8. Lavandula 'Lavden 123' is suitable as an ornamental in a container or in the landscape.
9. Lavandula 'Lavden' maybe susceptible to frost damage.

BRIEF DESCRIPTION OF THE DRAWINGS

The accompanying drawings illustrate the distinguishing characteristics of the new lavender plant 'Lavden 123'. The drawings were made of 12-month-old plants grown out-of-doors in 14-centimeter containers.

The drawing on sheet 1 illustrates the entire plant in bloom from a side view perspective.

The drawing on sheet 2 is a close-up view of a flower spike. The drawings were made using conventional photographic techniques and although colors may appear different from actual colors due to light reflectance, they are as accurate as possible by conventional photography.

BOTANICAL DESCRIPTION OF THE PLANT

The following is a detailed description of the Lavandula cultivar named 'Lavden 123'. Data was collected in Arroyo Grande, Calif. from 12-month-old plants grown in 14-centimeter containers grown out-of-doors. Color determinations are made in accordance with The 2001 Royal Horticultural Society Colour Chart except where general color terms of ordinary dictionary significance are used. The growing requirements are similar to the species. Care should be taken to avoid over watering and excessively humid conditions. Under proper care no disease problems or conditions have been observed.

Botanical classification: Lavandula 'Lavden 123'.
Species: *dentata*.
Common name: Lavender.
Parentage: Lavandula 'Lavden 123' is a hybrid plant that resulted from the induced hybridization of the following parent plants:
*Female parent plant.*—*Lavandula dentata.*
*Male parent plant.*—*Lavandula dentata.*
Type: Aromatic perennial shrub.
Use: Ornamental in container or landscape.
Growth rate: Vigorous.
Habit: Rounded and bushy.
Height: 48 cm. in height.
Width: 56 cm. in width.
Hardiness: USDA Zone 10.
Propagation method: Plant is propagated by cuttings or tissue culture.
Root system: Fibrous.
Soil: Plant in well-drained soil.
Light levels: Plant in full sun.
Time to initiate roots: 21 to 36 days is needed to develop roots on an initial cutting.
Time to develop to a 14-centimeter container size: 3 months from a rooted cutting.
Branching habit: Erect, upright and semi-open.
Seasonal interest: Flowers in spring and summer.
Stem:
*Stem shape.*—Tetrahedral.
*Stem surface.*—Lanate.
*Stem color.*—N138A with corners that are 156D.
*Stem size.*—3 mm. in diameter and 35 cm. in length.
*Stem fragrance.*—Camphor scented.
Foliage:
*Arrangement.*—Leaves are arranged opposite one another along basal third of stems.
*Leaf division.*—Simple.
*Leaf shape.*—Pinnatilobate.
*Margins.*—Crenate and slightly revolute.
*Apices.*—Rounded.
*Base.*—Attenuate.
*Attachment.*—Sessile.
*Color of leaves* (*adaxial surface*).—189A.
*Color of leaves* (*abaxial surface*).—189B.
*Leaf surfaces* (*adaxial and abaxial surfaces*).—Lanate.
*Venation.*—Mid vein is depressed on the adaxial surface and protruding on abaxial surface.
*Vein color* (*both surfaces*).—189C.
*Internodes.*—1.5 cm. between nodes.
*Foliar fragrance.*—Camphor scented.
*Leaf length.*—4 cm. in length.
*Leaf width.*—0.25 cm. in width.
Flower:
*Type of inflorescence.*—Spike.
*Size of inflorescence.*—8.50 cm in length and 2 cm in width.
*Shape of inflorescence.*—Cylindrical to cone-shaped with sterile bracts.
*Peduncles.*—22 cm in height and 3 mm in width.
*Peduncle color.*—N138B.
*Bud dimensions.*—6 mm. in height and 3 mm. in width.
*Bud color.*—96B.
*Bud surface.*—Lanate.
*Flower shape.*—Tubular.
*Flower diameter.*—3 mm. in diameter.
*Petals.*—Five in number.
*Corolla color.*—96A.
*Petals fused or unfused.*—Fused.
*Corolla tube depth.*—6 mm. in depth.
*Corolla tube color.*—N155A.
*Calyx color.*—138A with dark veins the color 83A.
*Calyx surface.*—Lanate.
*Basal fertile bract shape.*—Reniform.
*Basal fertile bract dimensions.*—9 mm. in height and 12 mm. in width.
*Basal fertile bract color.*—191B with margins and veins tinged N82B.
*Basal fertile bract apex.*—Rounded.
*Basal fertile bract base.*—Truncate.
*Basal fertile bract surface.*—Lanate.
*Number of basal fertile bracts per inflorescence.*—10 in number.
*Sterile bract shape.*—Deltoid.
*Number of sterile bracts per inflorescence.*—15 in number.
*Sterile bract margins.*—Pubescent.
*Sterile bract length.*—10 mm. in length.
*Sterile bract width.*—9 mm. in width.
*Sterile bract apex.*—Cuspidate.
*Sterile bract base.*—Cuneate.
*Sterile bract colour.*—N82B.
*Fragrance.*—Camphor scented.
*Blooming period.*—April to July.
Reproductive organs:
*Stamens.*—Four in number.
*Pistil.*—One in number.
*Dimensions of pistil.*—4 mm. in length and less than 0.25 mm. in diameter.
*Dimensions of stamens.*—3 mm. in length and less than 0.25 mm. in diameter.
*Color of pistil.*—155B.
*Color of stamen.*—155B.
*Color of stigma.*—200A.
*Ovary dimensions.*—0.50 mm. in height and 0.50 mm. in width.
*Ovary shape.*—Globose.
*Ovary color.*—138A.
*Ovary position.*—Superior.
Seed:
*Amount.*—2–5 seeds per capsule.
*Size.*—Minute.
*Shape.*—Oval.

I claim:

1. A new and distinct variety of Lavandula plant named 'Lavden 123' as described and illustrated.

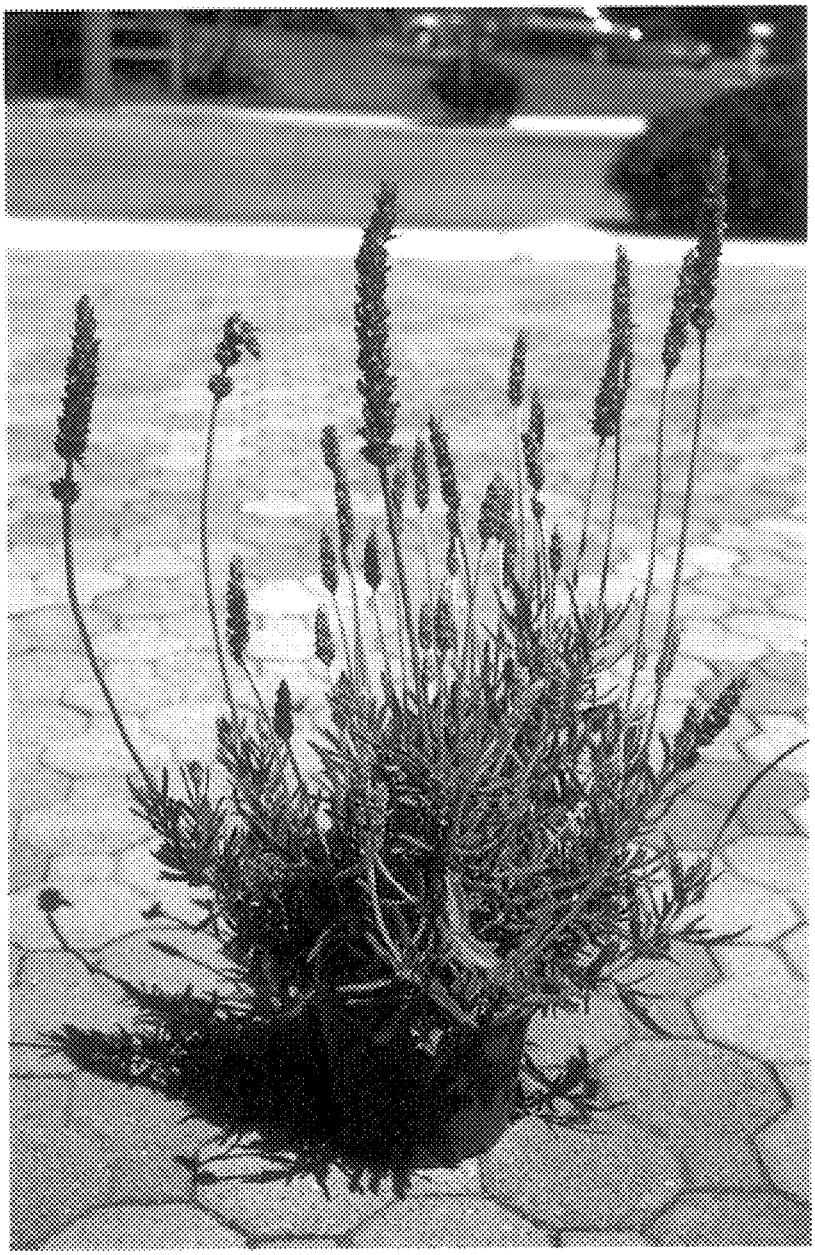

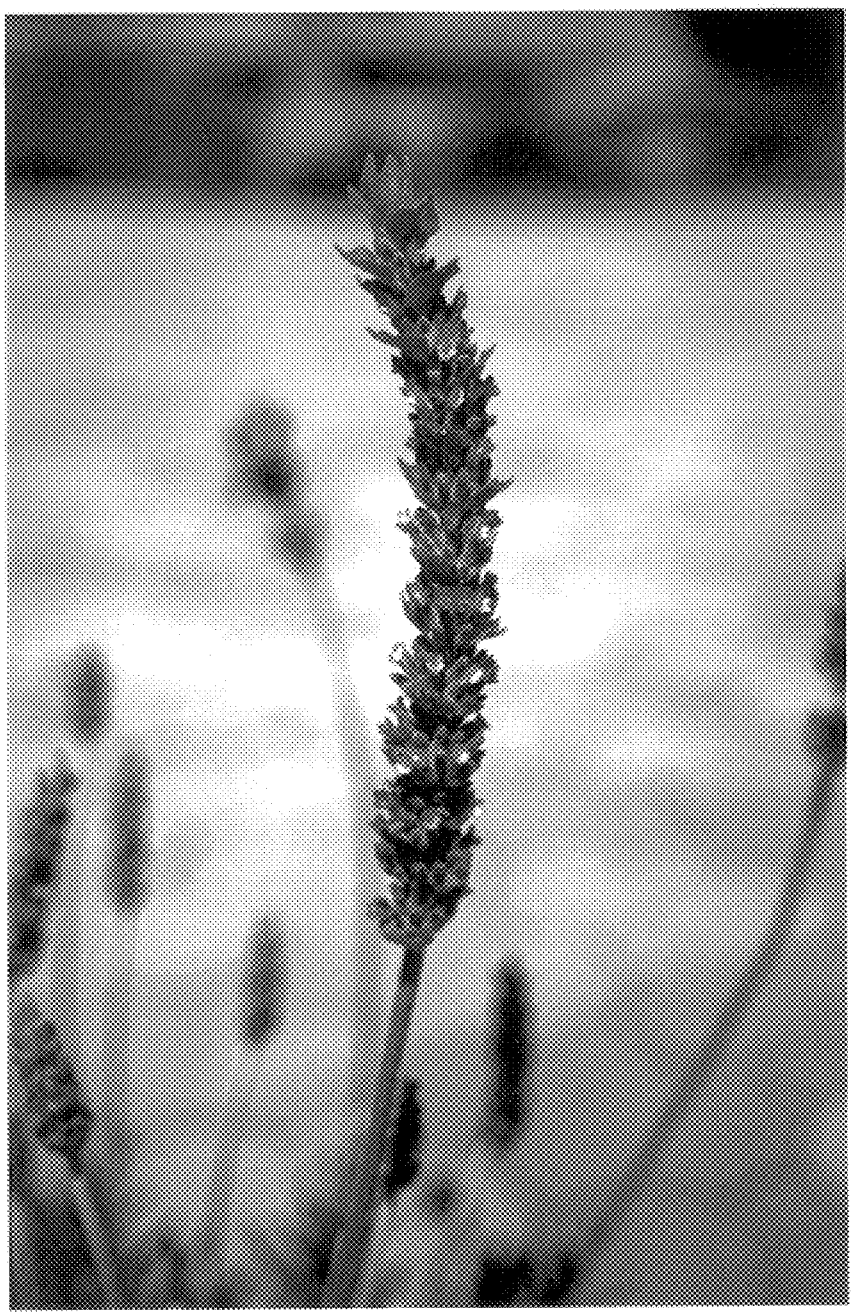

* * * * *